(12) United States Patent
Huang et al.

(10) Patent No.: US 8,568,434 B2
(45) Date of Patent: Oct. 29, 2013

(54) LANCING DEVICE

(75) Inventors: Mao-Sung Huang, Dali (TW);
Kuang-Li Huang, Dali (TW); Thomas Michel, Zurich (CH); Marita Larsson, St. Gallen (CH)

(73) Assignee: Bionime Corporation, Dali (TW)

( * ) Notice: Subject to any disclaimer, the term of this patent is extended or adjusted under 35 U.S.C. 154(b) by 561 days.

(21) Appl. No.: 12/250,971

(22) Filed: Oct. 14, 2008

(65) Prior Publication Data

US 2010/0094324 A1 Apr. 15, 2010

(51) Int. Cl.
*A61B 17/32* (2006.01)
(52) U.S. Cl.
USPC .......................................................... 606/182
(58) Field of Classification Search
USPC ........... 606/181, 172, 182, 183; 600/583, 167
See application file for complete search history.

(56) References Cited

U.S. PATENT DOCUMENTS

| 7,235,056 | B2 * | 6/2007 | Duchon et al. | 600/583 |
| 7,329,227 | B2 * | 2/2008 | Schramm | 600/567 |
| 2005/0090850 | A1 * | 4/2005 | Thoes et al. | 606/182 |
| 2008/0082116 | A1 * | 4/2008 | Lathrop et al. | 606/181 |

FOREIGN PATENT DOCUMENTS

EP 0115388 A1 8/1984

* cited by examiner

*Primary Examiner* — Ryan Severson
*Assistant Examiner* — Anh Dang
(74) *Attorney, Agent, or Firm* — Volpe and Koenig, P.C.

(57) ABSTRACT

A lancing device for ejecting a lancet having a pricking element protruding therefrom along an ejection axis is provided. The lancing device includes a front cap having an opening facing against an object to be pricked, a lancet holder slideable between a cocked position and a pricking position, and a safety switch moveable between a safety position and a passing position, wherein the pricking element extends beyond the opening when the lancet is ejected; the safety switch prevents the lancet holder form being cocked when the safety switch is in the safety position, and the safety switch allows the lancet holder to be cocked and moved when the safety switch is in the passing position.

17 Claims, 11 Drawing Sheets

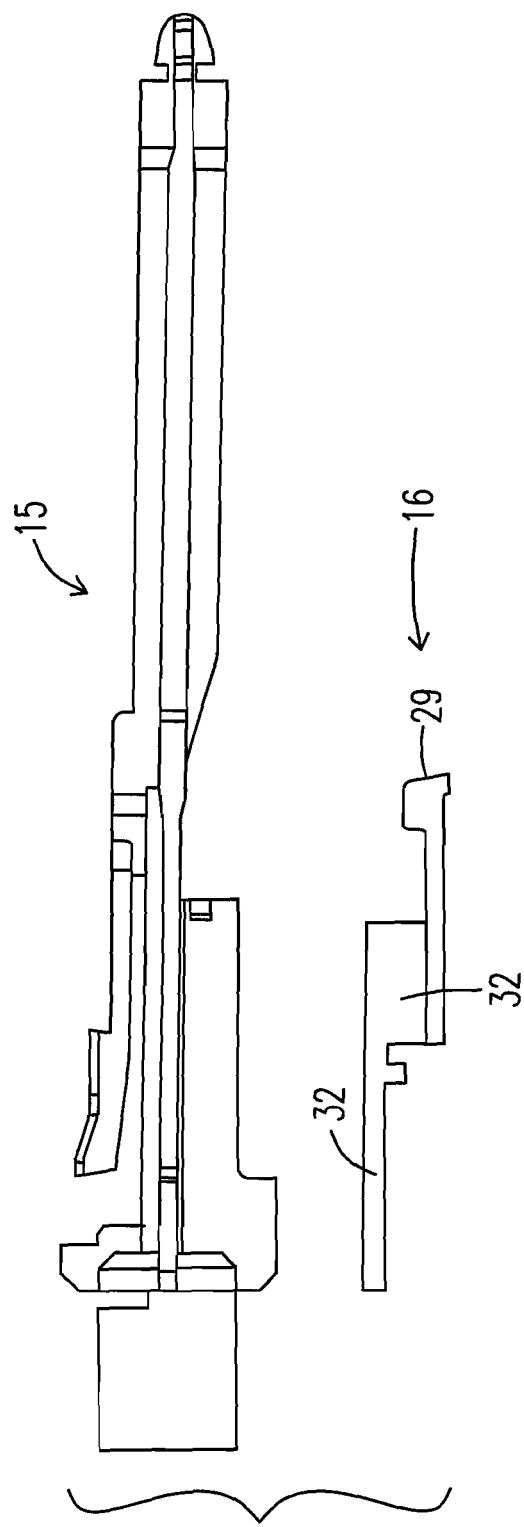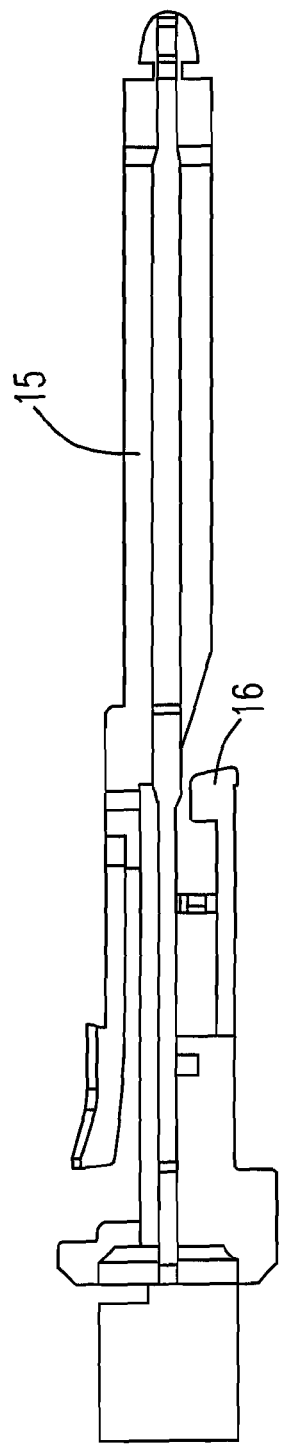
Fig. 10
Fig. 11

LANCING DEVICE

FIELD OF THE INVENTION

The present invention relates to a lancing device for ejecting a lancet according to the preamble of the independent claims.

BACKGROUND OF THE INVENTION

Many medical procedures in use today require a relatively small sample of blood, in the range of 5-50 µl. Normally such a sample is obtained by lancing or piercing the skin at a selected location, such as the finger, to enable the collection of 1 or 2 drops of blood. With the advent of home use tests such as self monitoring of blood glucose, there is a requirement for a simple and safe procedure which can be performed by a person needing to test.

Lancets in conventional use generally have a rigid body and a sterile pricking element, for example a needle, which protrudes from one end. The lancet may be used to pierce the skin, thereby enabling the collection of a blood sample from the opening created. The blood is transferred to a test device or collection device. Blood is most commonly taken from the fingertips, where the supply is generally excellent. However, blood can also be taken of alternate sites, such as earlobes and limbs.

To reduce the anxiety of piercing the skin and to guarantee a reproducible penetration result many spring loaded lancing devices have been developed.

The lancing device according to the present invention comprises a lancet holder, which is slideable in a housing member between a cocked position and a pricking position. In use the lancet holder carries a lancet which comprises a pricking element protruding there from along an ejection axis. The lancing device further comprises a front cap, which has an opening against which the object to be pricked is to be placed. The pricking element extends through the opening when the lancet is ejected.

Typically the lancet holder is axially slideable along the main axis of a generally tubular housing in forward direction into the pricking position and in backward direction for being loaded.

Conventional lancing devices, as for example disclosed in EP 0 115 388, typically require a user to put a lancet in a socket of a lancing device, arm the lancing device by latching the lancet holder in a retracted position, urge the lancing device against a target site, and then press a release button or other switch to manually activate the lancing device such that a lancet within the device is launched (also referred to as "fired") towards the target site. The lancet then penetrates the target site, thereby creating an opening for the expression of a bodily fluid sample.

After the lancet pierces the skin, a bounce back spring retracts the lancet to a safe position within the device. Now the lancet can be removed from the lancing device.

Typical lancing devices have a removable front cap, preferably also suited for adjusting the penetration depth. Once the front cap is removed the used lancet can be taken out of a socket of the lancet holder and a new lancet can be put in. When the front cap is removed from the body of the lancing device, the pricking element is exposed and there is a certain risk of injury and of contamination for the person who removes or changes the lancet. Known lancing devices generally are not protected from being fired unintentionally.

Even though many improvements have been made, the handling of the known lancing devices is still complicated for the user and there still is a risk of injury and contamination while replacing used lancets. It is the object of the present invention to overcome the drawbacks of the known devices, in particular to facilitate the change of the lancet, to prevent unintentional lancing and to provide a safe handling, especially of a lancing device with a used lancet.

SUMMARY OF THE INVENTION

According to a first aspect of the invention the lancing device possesses a safety switch. Said safety switch is moveable between a safety position, in which it prevents the lancet holder from being cocked and a passing position, in which it does not prevent cocking and/or movement of the lancet holder.

When the safety switch is in the safety position and thus the lancet holder is prevented from being cocked, the lancet cannot be fired from a cocked position with a high speed. By operating the safety switch the user can control the ability of the lancing device of firing the lancet.

The safety switch can for example be brought into the safety position, when the lancet was fired once and shall be changed. The risk for the person changing the lancet of being hit accidentally by the lancet is thereby reduced. Furthermore in a state, where the housing member is open to change the lancet, the lancet cannot be ejected by an unintended firing.

The safety switch may prevent the lancet holder from being cocked for example by blocking the movement of the lancet holder into the cocked position or by preventing latching of a clutch member on the lancet holder in a corresponding member of the housing.

When any movement of the lancet holder is blocked in the safety position a person may easily remove a lancet from or place a lancet into the socket of the lancet holder. The positioning of the lancet relatively to the lancet holder is facilitated, when the lancet holder does not move. The top of a used lancet can easily be stuck into a protective cover, if the lancet holder does not back off.

According to a second aspect of the invention the lancing device comprises an ejection pin for pushing the lancet out of the lancet holder, preferably in combination with the safety switch as described above. The ejection pin is moveable with respect to the lancet holder. The lancing device further comprises an ejection switch which is moveable between an ejection position, in which it allows relative movement of the ejection pin and the lancet holder, and a loading position, in which it does not affect a coupled movement of the ejection pin and the lancet holder.

For ejection of the lancet the ejection pin is used to push the lancet out of the socket of the lancet holder, thus there is no need for a person touching the lancet after use, especially the part of the lancet where the pricking element or needle protrudes. Preferably the ejection pin is arranged at the lancet holder and can protrude into the socket when the lancet shall be pushed out.

According to this aspect of the invention the lancing device comprises an ejection switch with two positions. In the first position, the so called ejection position, the ejection pin can be moved relatively to the lancet holder and the lancet can be pulled off the socket of the lancet holder.

The ejection switch may also take a second position, the so called loading position, in which the movement of the ejection pin and the lancet holder are coupled. In this position a lancet generally rests in the socket of the lancet holder.

In a preferred embodiment the ejection switch can be set in a loading position, in which it does not affect the movement of the ejection pin, especially along with a backward movement of the lancet holder.

In the ejection position the ejection switch provides a blocking of the movement of the ejection pin with respect to the housing of the lancing device. When the lancet holder is pulled backward, it is moved with respect to the ejection pin, which rests in its forward position and pushes the lancet out of the socket.

If the ejection switch is in the loading position and the lancet holder is pulled back in this position, the ejection pin moves along with the lancet holder and a lancet, being held in the socket, is also retracted. Thus the lancet holder can be pulled in the cocked position while carrying a lancet and the lancing device is loaded and ready to fire.

The backward movement of the lancet holder can both be used for loading the lancing device and for ejecting a used lancet.

Preferably the safety switch and/or the ejection switch are mounted on a switch member. More preferably the safety switch and the ejection switch are mounted on the same switch member.

Since the safety and the ejection position are especially suitable for changing the lancet the safety switch and the ejection switch are then simultaneously either in the safety and ejection position or in the passing and loading position.

Preferably the switch member is arranged between an outer and an inner housing. On the one hand the switch member can be moved independently of the position of the lancet holder and on the other hand the switch member may affect elements of the inner housing to contact elements of the lancet holder. More preferably the switch member is a tubular element.

In an advantageous embodiment the switch member is axially slideable inside the housing, preferably the outer housing. Thus the switch can be in a first position, in which it is preferably placed in its most forward position and in a second position, in which it is preferably in its most backward position.

In a further advantageous embodiment the lancing device comprises a safety spring for pushing the switch member, preferably into the ejection direction. Thus the switch member has a preferred position and the safety switch and/or the ejection switch also have a preferred switch position.

In a preferred embodiment the front cap is removable. The safety switch is brought into the safety position and/or the ejection switch is brought into the ejection position when the front cap is removed. Thus as soon as the lancing device is opened, for example for taking a used lancet or placing a new lancet, the safety switch and/or the ejection switch take the position, which is appropriate for changing the lancet.

In an advantageous embodiment the safety switch is held back in the passing position by the front cap and/or the ejection switch is held back in the loading position by the front cap, preferably against the spring force of a safety spring, as long as the front cap is attached. Thus the safety and/or ejection switch is operated by the removeable cap. Since the user anyway attaches the front cap after changing the lancet the safety and/or ejection switch is brought into the appropriate state automatically without any obligation for the user to separately operate the safety and/or ejection switch. Preferably the cap has a stopping face which presses the switch member is backward direction as long as the cap is attached. When the cap and thus the stopping face are removed the safety spring may actuate the switch member in ejection direction. The switch member can take the most forward position and the safety switch is in the safety position and/or the ejection switch is in the ejection position.

The lancing device according to the present invention may further comprise an operating means, especially a means for releasing the lancet holder from the cocked position. The lancing device is designed is such a way that when the safety switch is in the safety position it prevents the movement of the lancet holder towards the cocked position depending on the operation of the operating means, in particular as long as the operating means is not operated.

Alternatively the lancet holder may rest cocked in the forward position and is not moveable in the backward direction until the operating means are operated.

The means for releasing the lancet holder from the cocked position may be a push button arranged on the outside of a tubular body of the lancing device. Alternatively it may be a push button on one of the ends of the lancing device, it may also be turning knob, a lever, a touch field or any other operating element.

The means for releasing the lancet holder from the cocked position therefore not only may release the lancet holder from the cocked position. It also may allow the movement of the lancet holder towards the cocked position even if the safety switch is in the safety position. The lancet holder may preferably be moved in a backward position when the lancet has been fired once and is used. A backward movement of the lancet holder without achieving the cocked position may be useful for ejecting the lancet, when for example the ejection switch prevents the backward movement of the ejection pin along with the lancet holder.

In a preferred embodiment of the invention the front cap has to be removed for changing the lancet. When the cap is removed of the lancing device after firing the lancet, the switch member is pressed in ejection direction by a safety spring and brings the safety switch into the safety position and the ejection switch into the ejection position.

Once the cap is removed and the safety switch is in safety position, the lancet holder cannot be moved backwards into the cocked position. Thus there is no uncontrolled movement of the lancet bearing the risk of a sudden and accidental contact between the pricking element and the user. If the user wants to take off the lancet there is no need of touching the lancet. The user only presses the release button to allow a backward movement of the lancet holder and retracts a loading means coupled with the lancet holder in the same way he would do if he wants to load the lancing device. Thereby the user pulls the lancet holder backwards in the direction of the cocked position.

The safety switch still is in the safety position prevents the lancet holder from being cocked, for example by preventing a clutch element of the lancet holder to be latched at a locking face of the housing member. At the same time the ejection switch still is in the ejection position and prevents the ejection pin from being moved together with the lancet holder. Thus when the lancet holder is pulled back the ejection pin rests in its forward position and pushes the lancet out of the socket of the lancet holder.

Afterwards the user may let off the loading means and the release means. The lancet holder comes back to the front of the lancing device and is still prevented from being moveable in backward direction by the safety switch as long as the front cap is open. The user can put a new lancet into the socket of the lancet holder, the lancet holder not backing off when the lancet is pressed into the socket.

When the front cap is attached, the switch means again is brought into backward position. The safety switch thereby is brought into the passing position and the ejection pin is brought into the loading position. The lancing device is ready to be loaded and to be fired.

In an advantageous embodiment of the invention the lancing device comprises an outer housing and an inner housing. The inner housing comprises a first cantilever beam for engagement with a stopping face of a clutch element of the lancet holder and/or the inner housing comprises a second cantilever beam for engagement with a stopping face of the ejection pin. Thus the safety switch and/or the ejection switch may affect elements of the lancet holder via a cantilever beam of the inner housing. The position of the safety switch and/or of the ejection switch, especially when arranged on a safety switch, is completely independent from the position of the lancet holder and of the movement of the lancet holder.

Preferably the switch member is arranged between the outer housing and the inner housing. The switch member and thereby the safety switch and/or the ejection switch are shielded by the outer housing, and thus for example protected from being soiled or collecting dust, what could have a negative effect on the movement of the switch element.

According to a further aspect of the invention the lancing device comprises a loading member for moving the lancet holder in the cocked position and an ejection pin for pushing the lancet out of the lancet holder. The ejection pin is moveable with respect to the lancet holder. The lancing device farther comprises a mode switch member for switching between a using state, wherein operating the loading member provides a cocking of the lancet holder, and an exchange state wherein operating the loading member provides an ejection of a lancet off the lancet holder.

The loading member of the lacing device on the one hand can be used to bring the lancing device in a ready-to-fire state, when the switch member is in the using state, on the other hand the same loading member serves as an ejection tool. The lacing device therefore has no unnecessary operating elements and can be constructed in a compact and cost-efficient way. There is no need for separate security elements preventing unintended operation, when the lancing device is not in the appropriate state.

More preferably the mode switch member is a switch member and comprises a safety switch and an ejection switch as described above.

In a preferred embodiment of the lancing device with a mode switch member the lancing device further comprises a removable front cap. The lacing device is construed such that the switch member is brought into the using state, when the front cap is attached and the mode switch member is brought into the exchange state, when the front cap is removed.

The switch member thus is operated automatically by placing the front cap.

According to a further aspect of the invention the lancing device, preferably as described above, comprises an outer housing and an inner housing, the inner housing comprises at least two guide tracks, which guide at least two corresponding guide ribs being arranged on the lancet holder.

When the lancet held in the lancet holder is propelled in the puncture direction, it should perform a stable and smooth movement at high velocity along a predetermined puncturing path to reduce the pain. The guiding of the guide ribs in the guide tracks prevents rotational components of the movement and reduces vibrations during forward movement.

Preferably the inner housing comprises four guide tracks, which guide four corresponding guide ribs in the lancet holder. The guidance if the lancet holder is stabilized in perpendicular lateral directions and the resulting lateral tolerances are much smaller compared with a cylindrical guidance. A rectilinear advancement of the lancet holder reduces the pain during the needle insertion.

Additional objects and advantages of the invention will be set forth in the following descriptions with reference to the accompanying drawings, in which:

BRIEF DESCRIPTION OF THE DRAWINGS

FIG. 10 is a side view of a lancet holder and an ejection pin;
FIG. 11 is a side view of a lancet holder with an ejection pin.

DETAILED DESCRIPTION OF THE PREFERRED EMBODIMENT

The embodiments described below are merely exemplary and are not intended to limit the invention to the precise forms disclosed. Instead, the embodiments were selected for description to enable one of ordinary skill in the art to practice the invention.

Figure 1:
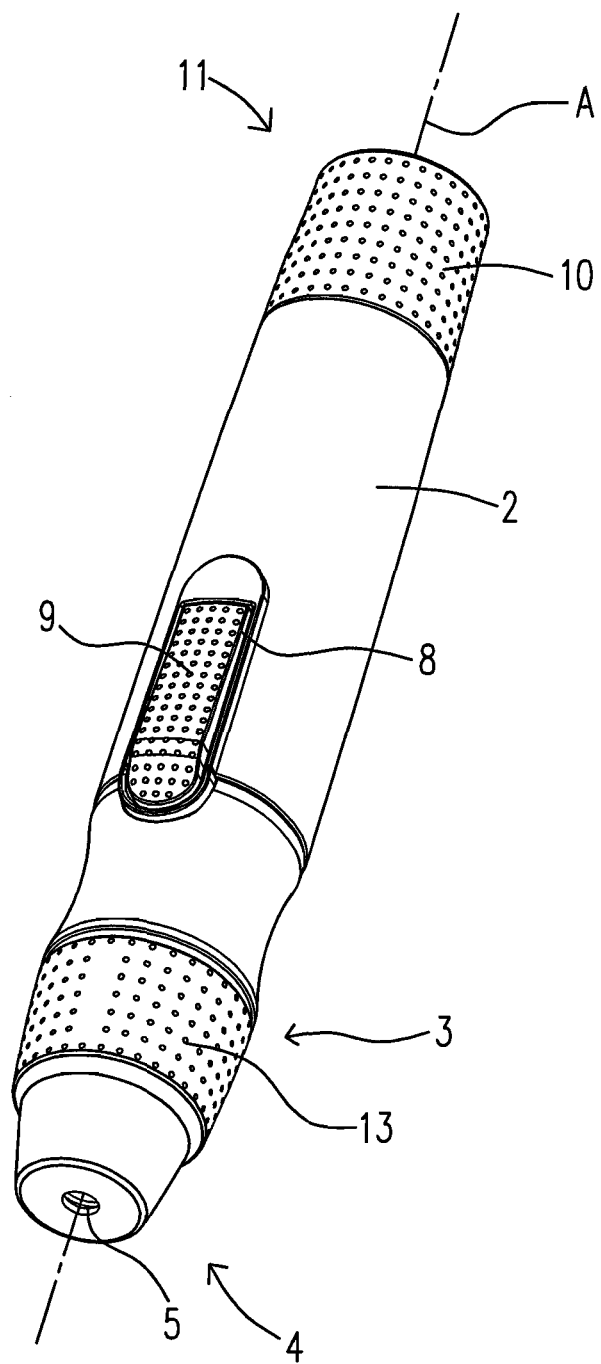
FIG. 1 is a perspective view of a lancing device.

FIG. 1 shows a perspective view of a lancing device 1. The lancing device 1 comprises an elongated outer housing 2 extending along the main axis A of the device 1. A removable cap 3 is disposed at the front end 4 of the housing 2 and has an exit opening 5 for the pricking tip 6 of a lancet 7, not shown in the figure.

The housing includes an orifice 8 which provides access to a release button 9 that is used to fire a lancet 7. A loading member 10 extends from the backward end 11 of the housing 2 and is used to arm the lancing device 1 prior to firing the lancet 7 with the release button 9.

The removable cap 3 comprises a cap holder 12 and a revolvable outer cap 13, by which the penetration depth can be adjusted in a manner known to those skilled in the art.

Figure 2:
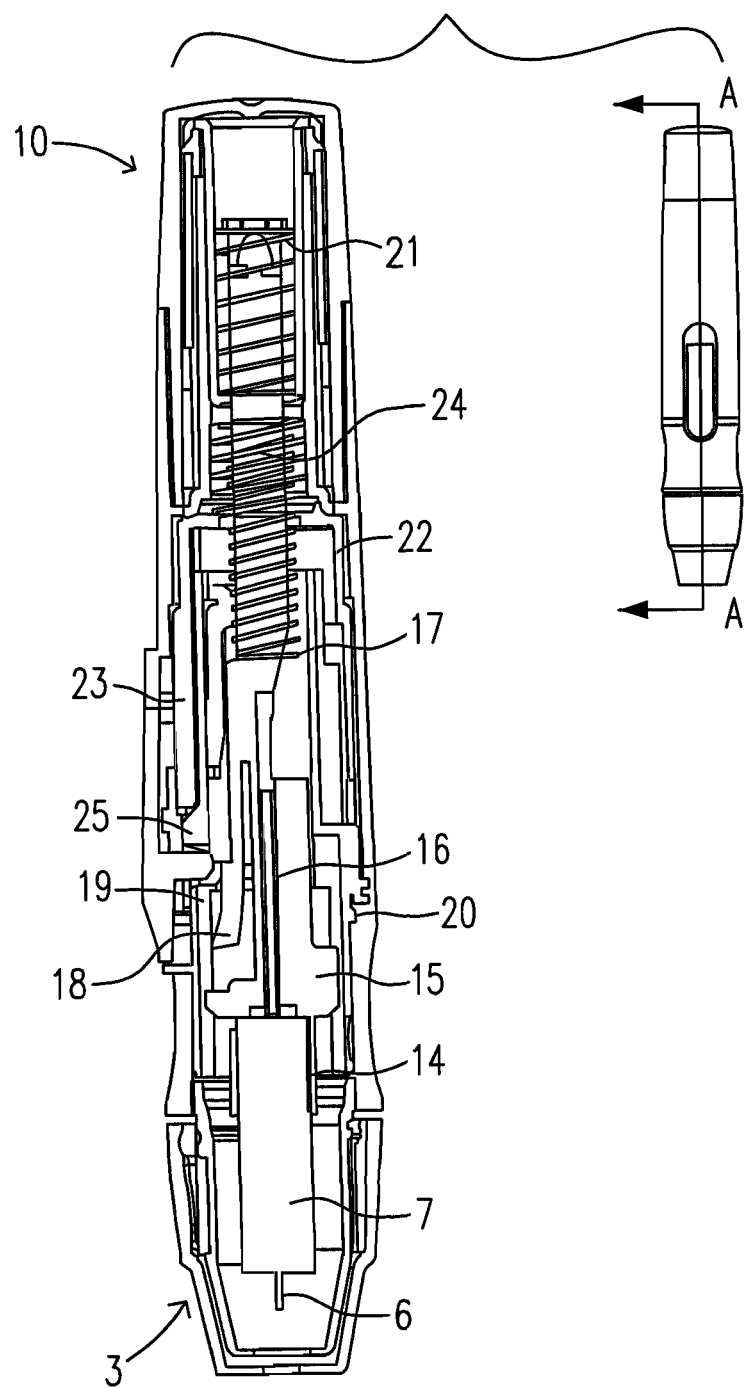
FIG. 2 is a cross sectional side view of the lancing device in FIG. 1, along a plane AA, with a safety switch in a passing position.

FIG. 2 shows a cross sectional side view of lancing device 1 along a plane AA. A lancet 7 is mounted in a socket 14 of a lancet holder 15. The lancet holder 15 is movable in a lancing direction D between a retracted position in which the lancet tip 6 does not extend outside of the end cap 3 and an extended position in which the lancet 7 is adapted to make a puncture having a certain puncture depth.

The lancet 7 is held by the socket 14 of the lancet holder 15 in such a fashion that the position of the tip 6 relative to the holder 15 is reproducibly the same when a new lancet 7 is inserted into the holder for subsequent blood withdrawal. The lancet holder 15 comprises an ejection pin 16, which has a position out of the socket 14 when a lancet 7 is positioned in the socket 14.

The pricking action is driven by a fire spring 17, which is loaded by pulling back the loading member 10 in opposition to its spring force.

After loading, the clutch element 18 of the lancet holder is locked in the cocked position using a locking face 19 on the inner housing 20 (not shown in detail in FIG. 2). The loading member 10 returns to the original position as shown in the figure.

An opening 5 of a front cap 3 is pressed against a body part in which a pricking is to be achieved in order to obtain a drop of blood. After pressing the release button 9 the lancet holder 15 then makes a puncturing motion to propel the lancet 7, held in the lancet holder 15, at high velocity along a predetermined puncturing path preferentially extending along the main axis A in the puncture direction D until its tip 6 exits from the opening 5 and penetrates into the body part. The lancet 7 then returns to its initial position inside the lancing device 1.

The return motion of the lancet holder 15, and thereby the lancet 7, as well as of the loading member 10 is driven by a return spring 21.

The lancing device 1 further comprises a switch member 22 with a safety switch 23. The switch member is held in backward position by the cap holder 12 against the spring force of a safety spring 24 (as may be better seen in FIG. 3). Since in this position the safety switch 23 does not prevent cocking and/or movement of the lancet holder it is in a so called "passing position".

The switch member is positioned between the inner housing 20 and the outer housing 2, such that the safety switch may affect a first cantilever beam 25 of the inner housing 20.

The lancet device 1 as shown in FIG. 2 is ready to be loaded by pulling the back bar 10, thus the switch member 22 is in the so called "using state".

Figure 3:
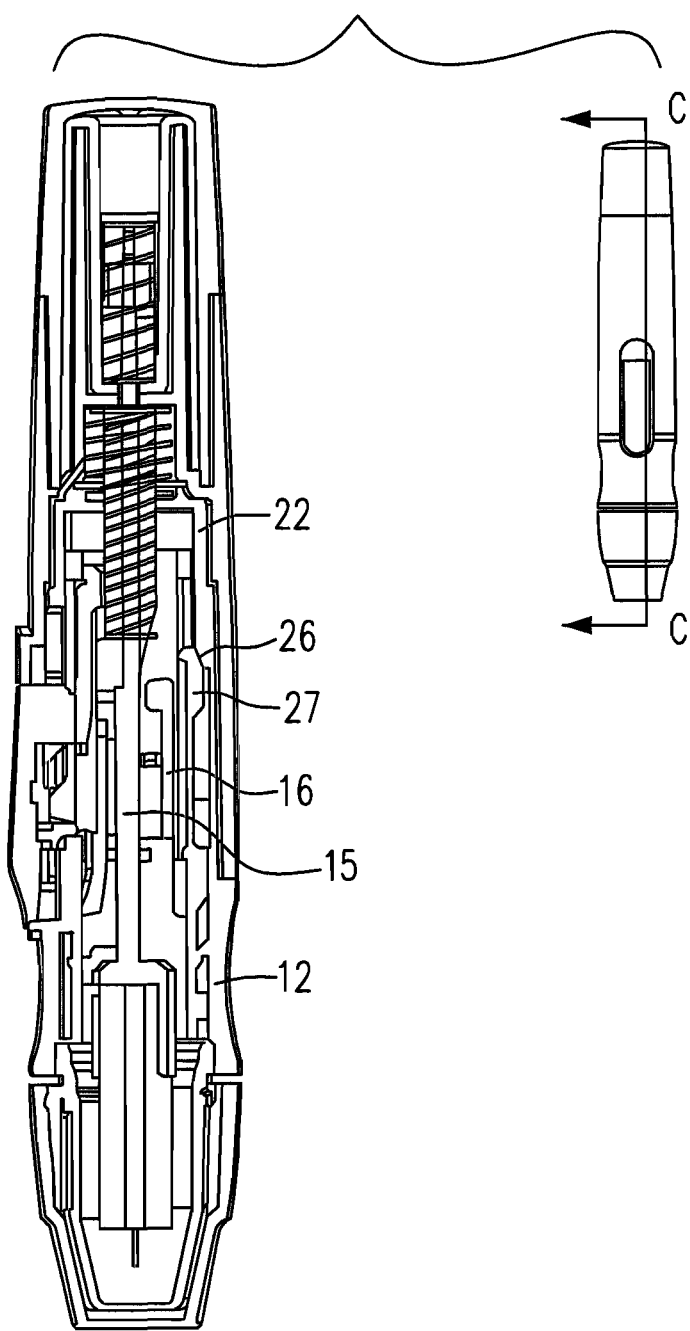
FIG. 3 is a cross sectional side view of the lancing device in FIG. 1, along a plane CC, with an ejection switch in loading position.

As presented in FIG. 3, which shows a cross sectional side view of a lancing device 1 along an axis CC, the switch member 22 also comprises an ejection switch 26 which may affect a second cantilever beam 27 of the inner housing 20.

In the position shown in the figure the ejection switch 26 does not affect a coupled movement of the ejection pin 16 and the lancet holder 15, which is necessary for avoiding the ejection of the lancet 7 off the lancet holder 15 and thus for loading the lancing device 1, thus the ejection switch 26 is the so called "loading position".

Figure 4:
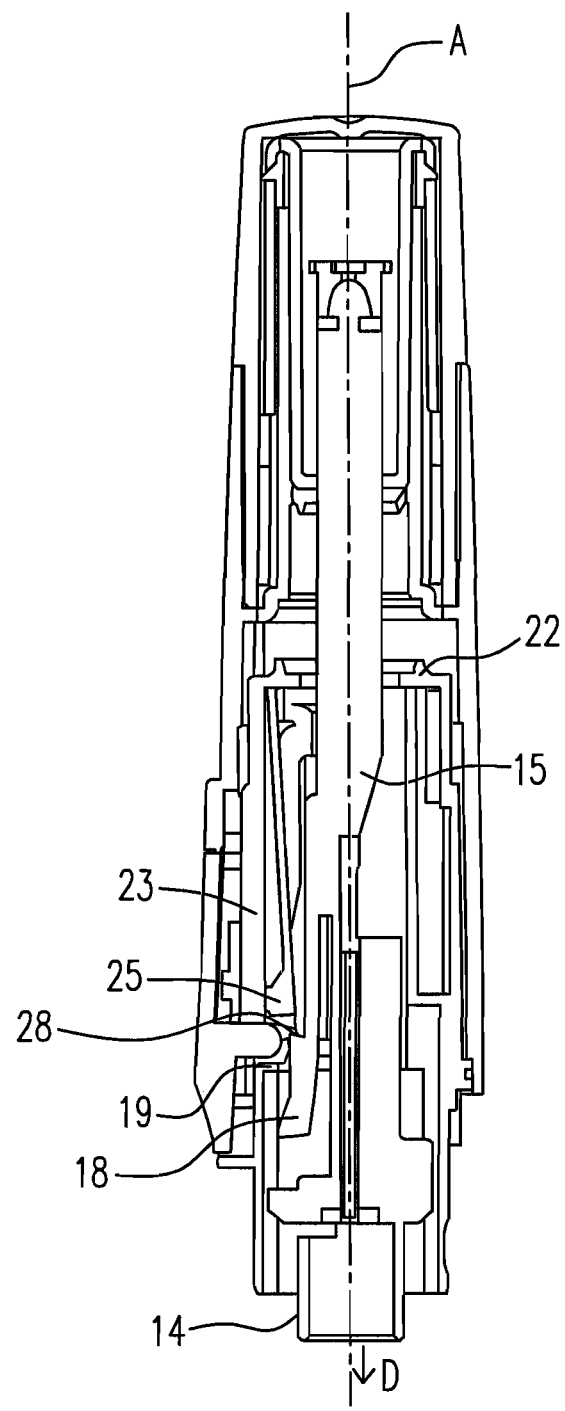
FIG. 4 is a cross sectional side view of the lancing device in FIG. 1, along a plane AA, without front cap and with the safety switch in a safety position.

FIG. 4 presents a cross sectional side view of the lancing device 1, along a plane AA, without front cap 3 and with the safety switch 23 in safety position. When the front cap 3 is removed, the switch member 22 is urged in pricking direction D by the safety spring 24 (not shown in the figure). The safety switch 23 thereby affects the first cantilever beam 25 which is inclined towards the main axis A and engages a stopping face 28 of a clutch element 18 of the lancet holder 15. In this state the lancet holder 15 cannot back off against the pricking direction D.

If a new lancet (not shown in FIG. 4) shall be put into the socket 14 of the lancet holder 15 the lancet holder 15 is restricted from backward movement, what makes the charging of the lancing device 1 comfortable and secure for a user.

Figure 5:
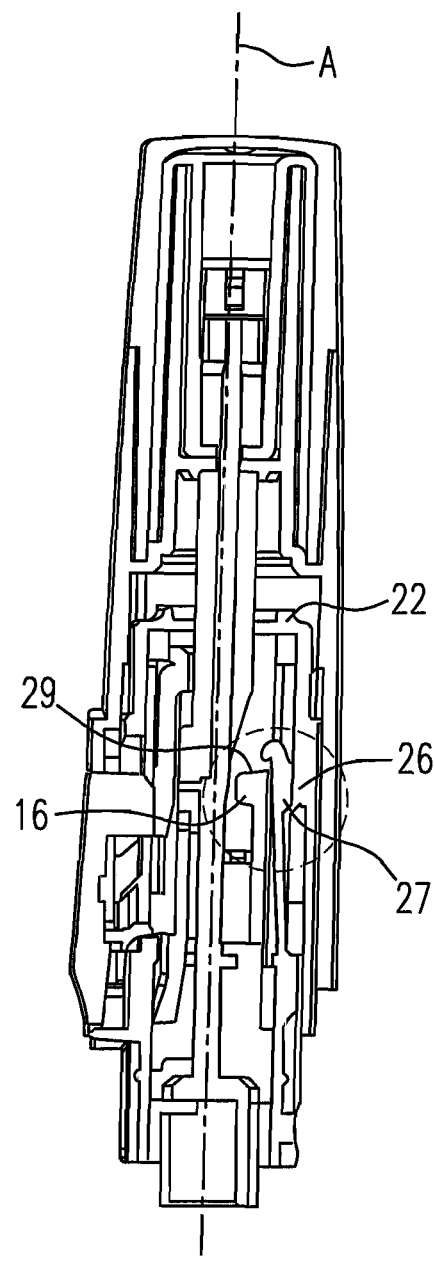
FIG. 5 is a cross sectional side view of the lancing device in FIG. 1, along a plane CC without front cap and with the ejection switch in ejecting position.

FIG. 5 presents a cross sectional side view of the lancing device 1, along a plane CC, without front cap 3.

As long as the front cap 3 remains removed, the switch member 22 is urged in pricking direction D. The ejection switch 26 thereby affects the second cantilever beam 27 which is also inclined towards the main axis A and which engages a stopping face 29 of the ejection pin 16 in a hooking manner. The ejection pin 16 is prevented from being moved along with the lancet holder 15, the ejection switch 26 thus is in the so called "ejection position".

Figure 6:
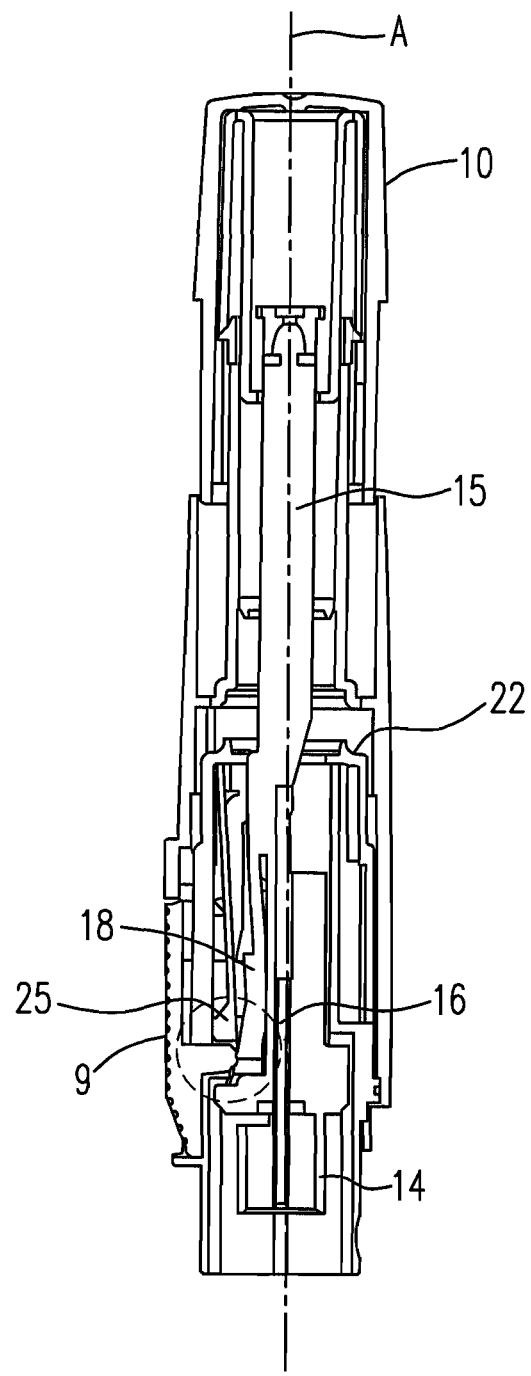
FIG. 6 is another cross sectional side view of the lancing device in FIG. 1, along a plane AA without front cap and with a loading member being pulled backwards.

As can be seen in FIG. 6, showing another cross sectional view of the lancing device 1, when the cap 3 is removed and the release button 9 is pressed, the clutch element 18 of the lancet holder 15 is urged towards the main axis A of the lancing device 1 and may pass the first cantilever beam 25, when the back bar 10 is pulled. Thus the lancet holder 15 can be retracted backwards.

In this position the safety switch 23 still prevents the lancet holder 15 from being cocked, because it does not allow the clutch element 18 to be hold by the locking face 19 in the inner housing 20, it is thus in the so called "safety position". Though the lancet holder 15 can be moved, it cannot be cocked.

Since the switch member 22 still is in forward position, the ejection switch still affects the second cantilever beam 25, which engages the ejection pin 16 (not shown in the figure). The ejection pin 16 thereby is prevented from being moved along with lancet holder 15. The ejection pin 16 rests in its forward position and penetrates the socket 14 of the lancet holder 15.

When a lancet 7 (not shown in the figure) is held in the socket 14 it is ejected by the ejection pin 16.

If the switch element 22 is in the forward position, pulling the loading member 10 does not result in loading the lancing device, because the lancet holder 15 cannot been cocked, but rather in ejecting a lancet from the lancet holder 15, the switch element 22 corresponds to a mode switch element 22 which is in the so called "exchange state".

Figure 7:
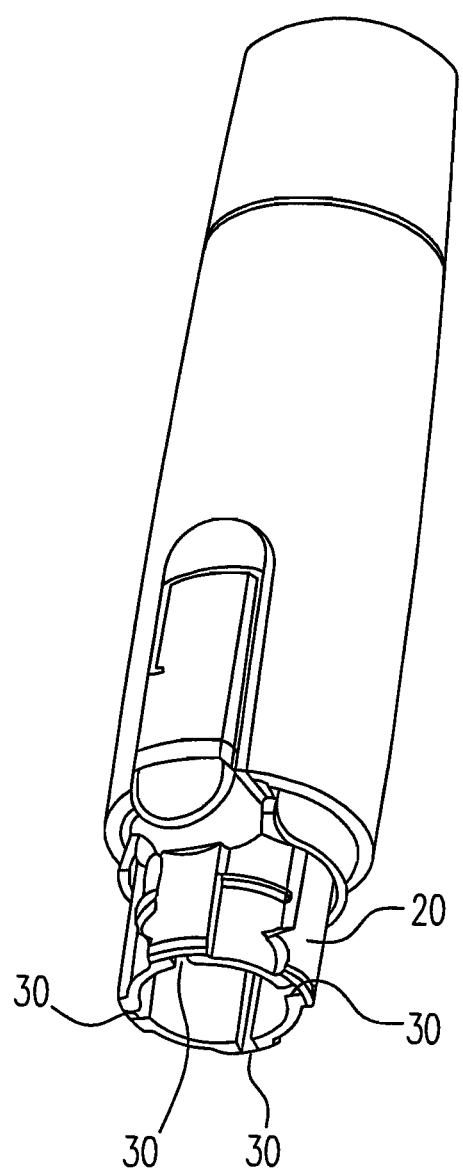
FIG. 7 is a perspective view of the lancing device without front cap.

FIG. 7 shows a perspective view of a lancing device 1 without front cap 3. On the inside of the inner housing 20 there are four guide tracks 30 for accommodating guide ribs 31 of the lancet holder 15.

Figure 8:
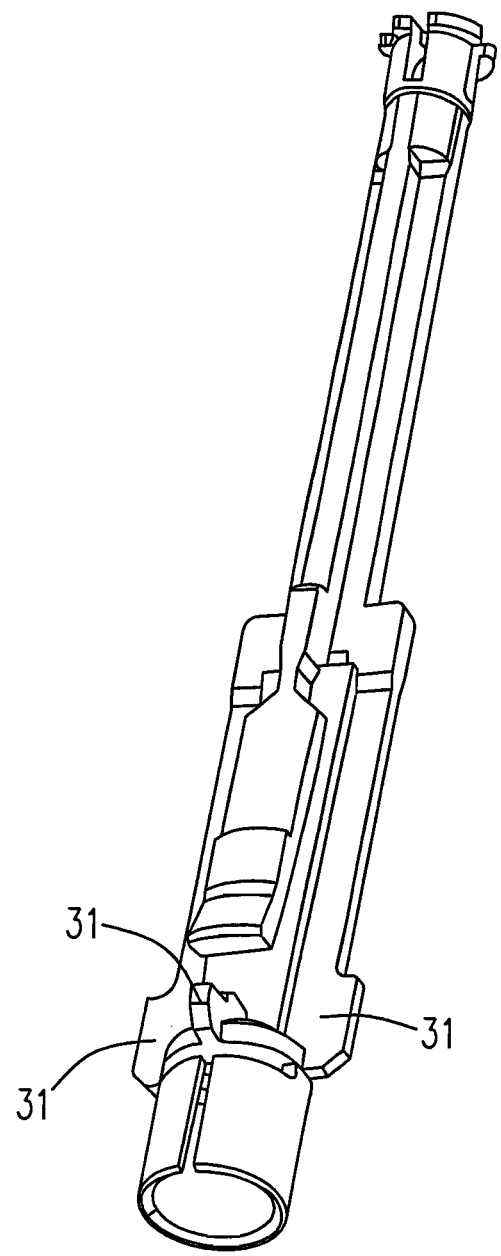
FIG. 8 is a perspective view of a lancet holder.

FIG. 8 shows a perspective view of a lancet holder 15 with four guide ribs. The guiding of the guide ribs 31 in the guide tracks 30 guarantees a stable and smooth movement of the lancet 7, when the lancet holder is propelled in lancing direction D.

Figure 9:
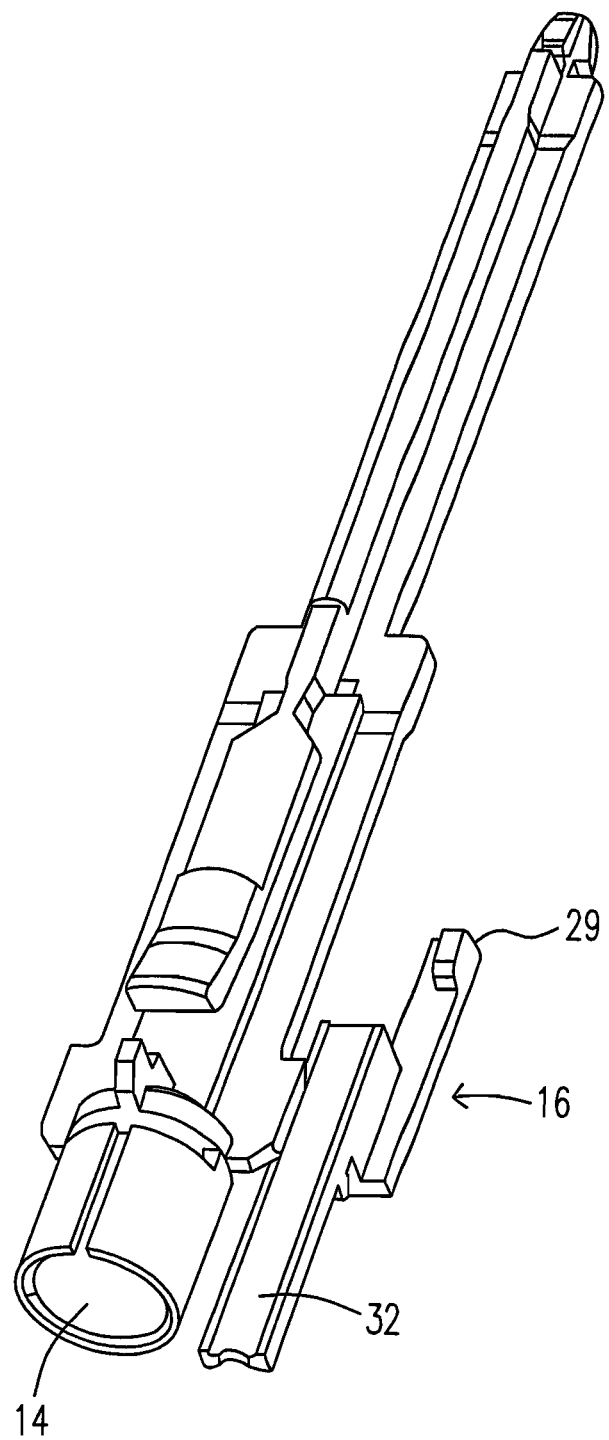
FIG. 9 is a perspective view of a lancet holder and an ejection pin.

FIG. 9 is a perspective view of the lancet holder 15 and the ejection pin 16, whereas FIG. 10 shows a side view of the lancet holder 15 and the ejection pin 16.

The ejection pin 16 has two parts. A first part 32 may protrude in the socket 14 to eject the lancet. A second part can be arranged on the outside of the socket 14 and comprises a stopping face for being hooked by the second cantilever beam 27 of the inner housing 20 not shown in the figure.

FIG. 11 is a side view of a lancet holder 15 with an ejection pin 16. The ejection pin 16 is plugged in the lancet holder 15 and lancet holder 15 and ejection pin 16 are moveable relatively to each other, such that the first part 32 of the ejection pin 16 may shifted to the inside of the socket 14.

Figure 12:
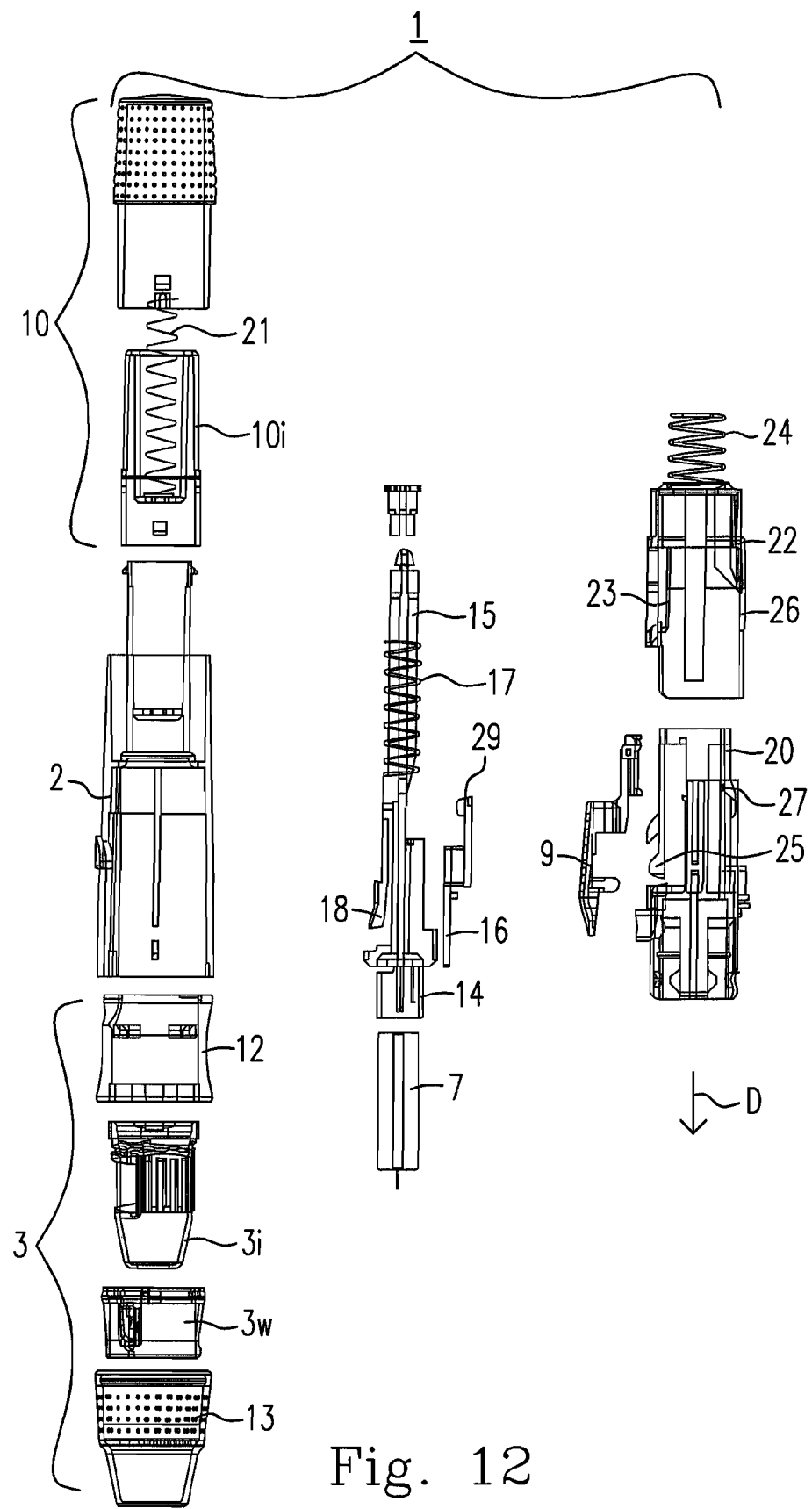
FIG. 12 is an exploded view on all parts of the lancing device.

FIG. 12 is an exploded view on all parts of the lancing device 1.

The outer body of the lancing device 1 consist of the outer housing 2, which accommodates a loading member 10, comprising an inner loading member 10i and a return spring 21. Fixable to the outer housing is a removable cap 3. The cap 3 is adapted to adjust the penetration depth and therefore comprises a preferable transparent turnable outer cap 13, a window cap 3w and an inner cap 3i.

The lancet 7 may be inserted into a socket 14 of a lancet holder 15, by which the lancet 7 may be activated when the fire spring 17 is loaded and released.

The lancet 7 may be ejected from the socket 14 by an ejection pin 16.

The clutch member 18 of the lancet holder 15 cooperates with parts of the inner housing 20. It may for example abut against a first cantilever beam 25 when the first cantilever beam 25 is pressed inwardly by the safety switch 23 of the safety member 22.

The safety member 22 further comprises an ejection switch 26, which may interact with a second cantilever beam 27 for holding the a stopping face 29 of the ejection pin 16.

The safety member 22 is actuated in lacing direction D by a safety spring 24.

Embodiments

1. A lancing device for ejecting a lancet having a pricking element protruding therefrom along an ejection axis, comprising a front cap having an opening facing against an object to be pricked, a lancet holder slideable between a cocked position and a pricking position, and a safety switch moveable between a safety position and a passing position, wherein the pricking element extends beyond the opening when the lancet is ejected; the safety switch prevents the lancet holder form being cocked when the safety switch is in the safety position, and the safety switch allows the lancet holder to be cocked and moved when the safety switch is in the passing position.

2. A lancing device as in Embodiment 1 further comprising an ejection pin pushing the lancet out of the lancet holder, and an ejection switch moveable between an ejection position and an loading position, wherein the ejection pin is moveable with respect to the lancet holder; the ejection switch allows a relative movement of the ejection pin and the lancet holder for ejecting the lancet when in the ejection position, and the ejection switch does not affect a coupled movement of the ejection pin and the lancet holder when in the loading position.

3. A lancing device as in Embodiment 2, wherein the ejection switch in the loading position affords a movement of the ejection pin.

4. A lancing device as in Embodiment 3, wherein the ejection pin moves along with a backward movement of the lancet holder.

5. A lancing device as in Embodiment 2 further comprising a mode switch member, wherein at least one of the safety switch and the ejection switch are mounted on the mode switch member.

6. A lancing device as in Embodiment 5, wherein the mode switch member is slidable along the ejection axis.

7. A lancing device as in Embodiment 5, further comprising a safety spring for pushing the mode switch member.

8. A lancing device as in Embodiment 2, wherein the front cap is removable and the ejection switch is brought in the ejection position by removing the front cap.

9. A lancing device as in Embodiment 2, wherein the ejection switch is held in the loading position by the front cap, and the front cap is urged against a spring force of a safety spring as long as the front cap is attached.

10. A lancing device as in Embodiment 2 further comprising an outer housing and an inner housing, wherein the lancet holder has a clutch element, and the inner housing includes a first cantilever beam engaging with a first stopping face of the clutch element, and a second cantilever beam engaging with a second stopping face of the ejection pin.

11. A lancing device as in Embodiment 1, wherein the front cap is removable and the safety switch is brought in the safety position by removing the front cap.

12. A lancing device as in Embodiment 1, wherein the safety switch is held in the passing position by the front cap, and the front cap is urged against a spring force of a safety spring as long as the front cap is attached.

13. A lancing device as in Embodiment 1 further comprising an operation means for releasing the lancet holder from the cocked position, wherein the safety switch being in the safety position prevents a movement of the lancet holder towards the cocked position as long as the operating means is not operated.

14. A lancing device as in Embodiment 1 further comprising a loading member moving the lancet holder in the cocked position, an ejection pin for pushing the lancet out of the lancet holder, and a mode switch member switching between a using state and an exchange state, wherein the ejection pin is moveable with respect to the lancet holder; the lancet holder is cocked by operating the loading member when the mode switch member is in the using state, and the lancet placed in the lancet holder is ejected by operating the loading member when the mode switch member is in the exchange state.

15. A lancing device as in Embodiment 14, wherein the front cap is a removable front cap, the mode switch member is brought in the using state when the front cap is attached, and the mode switch member is brought into the exchange state when the front cap is removed.

16. A lancing device as in Embodiment 1 further comprising an outer housing and an inner housing, wherein the lancet holder has at least two guide ribs, and the inner housing includes at least two guide tracks guiding the at least two guide ribs that correspond to the at least two guide tracks.

17. A lancing device for ejecting a lancet, comprising a lancet holder slideable between a cocked position and a pricking position, and a safety switch moveable between a safety position and a passing position, wherein the safety switch prevents the lancet holder form being cocked when the safety switch is in the safety position, and the safety switch allows the lancet holder to be cocked and moved when the safety switch is in the passing position.

18. A lancing device as in Embodiment 17 further comprising a front cap having an opening facing against an object to be pricked, an ejection pin pushing the lancet out of the lancet holder, and an ejection switch moveable between an ejection position and an loading position, wherein the pricking element extends beyond the opening when the lancet is ejected; the ejection pin is moveable with respect to the lancet holder; the ejection switch allows a relative movement of the ejection pin and the lancet holder for ejecting the lancet when in the ejection position, and the ejection switch does not affect a coupled movement of the ejection pin and the lancet holder when in the loading position.

19. A lancing device having a lancet holder and an ejection pin for ejecting a lancet, comprising an ejection switch moveable between an ejection position and a loading position, wherein the ejection switch allows a relative movement of the ejection pin and the lancet holder for ejecting the lancet when the ejection switch is in the ejection position, and the ejection switch does not affect a coupled movement of the ejection pin and the lancet holder when the ejection switch is in the loading position.

20. A lancing device as in Embodiment 19, wherein the lancet holder is slideable between a cocked position and a pricking position, and the ejection pin is used to push the lancet out of the lancet holder and is moveable with respect to the lancet holder.

While the invention has been described in terms of what is presently considered to be the most practical and preferred embodiments, it is to be understood that the invention needs not be limited to the disclosed embodiments. On the contrary, it is intended to cover various modifications and similar arrangements included within the spirit and scope of the appended claims which are to be accorded with the broadest interpretation so as to encompass all such modifications and similar structures.

What is claimed is:

1. A lancing device for ejecting a lancet having a pricking element protruding therefrom along an ejection axis, comprising:
   an outer housing;
   a front cap having an opening facing against an object to be pricked, the pricking element extending beyond the opening when the lancet is ejected;
   a lancet holder slideable between a cocked position and a pricking position along a lancing axis; and
   a safety switch rectilinearly moveable along the ejection axis between a safety position and a passing position for preventing an unintended ejecting of the lancet device, wherein the ejection axis is parallel to the lancing axis, the safety switch prevents the lancet holder from being cocked when the safety switch is brought in the safety position if the front cap is removed from the outer housing, and the safety switch allows the lancet holder to be cocked and moved when the safety switch is brought in the passing position if the front cap is attached to the outer housing, and the safety switch is disposed on the ejection axis.

2. A lancing device according to claim 1 further comprising:
   an ejection pin pushing the lancet out of the lancet holder, wherein the ejection pin is moveable with respect to the lancet holder; and
   an ejection switch moveable between an ejection position and an loading position, wherein the ejection switch allows a relative movement of the ejection pin and the lancet holder for ejecting the lancet when in the ejection position, and the ejection switch does not affect a coupled movement of the ejection pin and the lancet holder when in the loading position.

3. A lancing device according to claim 2, wherein the ejection switch in the loading position affords a movement of the ejection pin.

4. A lancing device according to claim 3, wherein the ejection pin moves along with a backward movement of the lancet holder.

5. A lancing device according to claim 2 further comprising a mode switch member, wherein at least one of the safety switch and the ejection switch are mounted on the mode switch member.

6. A lancing device according to claim 5, wherein the mode switch member is slidable along the ejection axis.

7. A lancing device according to claim 5, further comprising a safety spring for pushing the mode switch member.

8. A lancing device according to claim 2, wherein the front cap is removable and the ejection switch is brought in the ejection position by removing the front cap.

9. A lancing device according to claim 2, wherein the ejection switch is held in the loading position by the front cap, and the front cap is urged against a spring force of a safety spring as long as the front cap is attached.

10. A lancing device according to claim 2 further comprising an inner housing, wherein the lancet holder has a clutch element, and the inner housing includes:
   a first cantilever beam engaging with a first stopping face of the clutch element; and
   a second cantilever beam engaging with a second stopping face of the ejection pin.

11. A lancing device according to claim 1, wherein the safety switch is held in the passing position by the front cap, and the front cap is urged against a spring force of a safety spring as long as the front cap is attached.

12. A lancing device according to claim 1 further comprising an operation means for releasing the lancet holder from the cocked position, wherein the safety switch being in the safety position prevents a movement of the lancet holder towards the cocked position as long as the operating means is not operated.

13. A lancing device according to claim 1 further comprising:
   a loading member moving the lancet holder in the cocked position;
   an ejection pin for pushing the lancet out of the lancet holder, wherein the ejection pin is moveable with respect to the lancet holder; and
   a mode switch member switching between a using state and an exchange state, wherein the lancet holder is cocked by operating the loading member when the mode switch member is in the using state, and the lancet placed in the lancet holder is ejected by operating the loading member when the mode switch member is in the exchange state.

14. A lancing device according to claim 13, wherein the front cap is a removable front cap, the mode switch member is brought in the using state when the front cap is attached, and the mode switch member is brought into the exchange state when the front cap is removed.

15. A lancing device according to claim 1 further comprising an inner housing, wherein the lancet holder has at least two guide ribs, and the inner housing includes at least two guide tracks guiding the at least two guide ribs that correspond to the at least two guide tracks.

16. A lancing device for ejecting a lancet along an ejection axis, comprising:
   an outer housing;
   a removable front cap;
   a lancet holder slideable between a cocked position and a pricking position along a lancing axis, and including a clutch element;
   an ejection pin moveable with respect to the lancet holder;
   an inner housing including a first cantilever beam engaging with a first stopping face of the clutch element, and a second cantilever beam engaging with a second stopping face of the ejection pin; and
   a safety switch rectilinearly moveable along the ejection axis between a safety position and a passing position for preventing an unintended ejecting of the lancet device, wherein the ejection axis is parallel to the lancing axis, the safety switch prevents the lancet holder from being cocked when the safety switch is brought in the safety position if the removable front cap is removed from the outer housing, the safety switch allows the lancet holder to be cocked and moved when the safety switch is brought in the passing position if the removable front cap is attached to the outer housing, and the safety switch is disposed on the ejection axis.

17. A lancing device according to claim 16, wherein
the removable front cap has an opening facing against an object to be pricked, the ejection pin pushes the lancet out of the lancet holder, and the lancing device further comprises:
   a pricking element extending beyond the opening when the lancet is ejected; and
   an ejection switch moveable between an ejection position and an loading position, wherein the ejection switch allows a relative movement of the ejection pin and the lancet holder for ejecting the lancet when in the ejection position, and the ejection switch does not affect a coupled movement of the ejection pin and the lancet holder when in the loading position.

\* \* \* \* \*